United States Patent [19]

Krumme

[11] Patent Number: 4,485,816
[45] Date of Patent: Dec. 4, 1984

[54] SHAPE-MEMORY SURGICAL STAPLE APPARATUS AND METHOD FOR USE IN SURGICAL SUTURING

[75] Inventor: John F. Krumme, Woodside, Calif.

[73] Assignee: Alchemia, Palo Alto, Calif.

[21] Appl. No.: 277,112

[22] Filed: Jun. 25, 1981

[51] Int. Cl.³ .................. A61B 17/04; A61B 17/08; A61B 17/12
[52] U.S. Cl. .................. 128/334 R; 128/335; 128/325; 411/909; 227/DIG. 1
[58] Field of Search ............ 128/334 R, 334 C, 335, 128/335.5, 325, 326, 419 P, 92 B, 92 C, 92 CA, 92 R, 92 D, 92 G; 411/909; 3/1.7; 227/19, DIG. 1; 285/381

[56] References Cited

U.S. PATENT DOCUMENTS

| | | | |
|---|---|---|---|
| 3,606,592 | 9/1971 | Madurski et al. | 3/1.7 |
| 3,620,212 | 11/1971 | Fannon, Jr. et al. | 128/130 |
| 3,786,806 | 1/1974 | Johnson et al. | 128/92 D |
| 3,890,776 | 6/1975 | Wilson | 128/419 P |
| 3,913,444 | 10/1975 | Otte | 411/909 |
| 4,170,990 | 10/1979 | Baumgart et al. | 128/92 B |

FOREIGN PATENT DOCUMENTS 734439 5/1980 U.S.S.R. .................. 411/909

Primary Examiner—Kyle L. Howell
Assistant Examiner—C. W. Shedd
Attorney, Agent, or Firm—Howard L. Rose

[57] ABSTRACT

The staples are made of a material having the intrinsic property of shape memory, such that heating the material above a certain temperature known as the transition temperature causes any deformation introduced at temperatures below the transition temperature to be reversed, and the staple recovers fully to its shape prior to the deformation. By forming the staple into any desired closed position at a temperature above the transition temperature and then cooling the staple below the transition temperature before deforming it into an open position, the resulting staple will revert to its closed position when it is subsequently reheated above the transition temperature. Consequently, the staple can be used for surgical suturing by merely positioning it in contact with the tissues to be sutured and heating it sufficiently to cause it to penetrate and clinch the tissues together. A low-cost, lightweight surgical staple applicator utilizes a battery for heating the staples to produce closure, and is sterilizable by gamma radiation.

14 Claims, 9 Drawing Figures

FIG.1

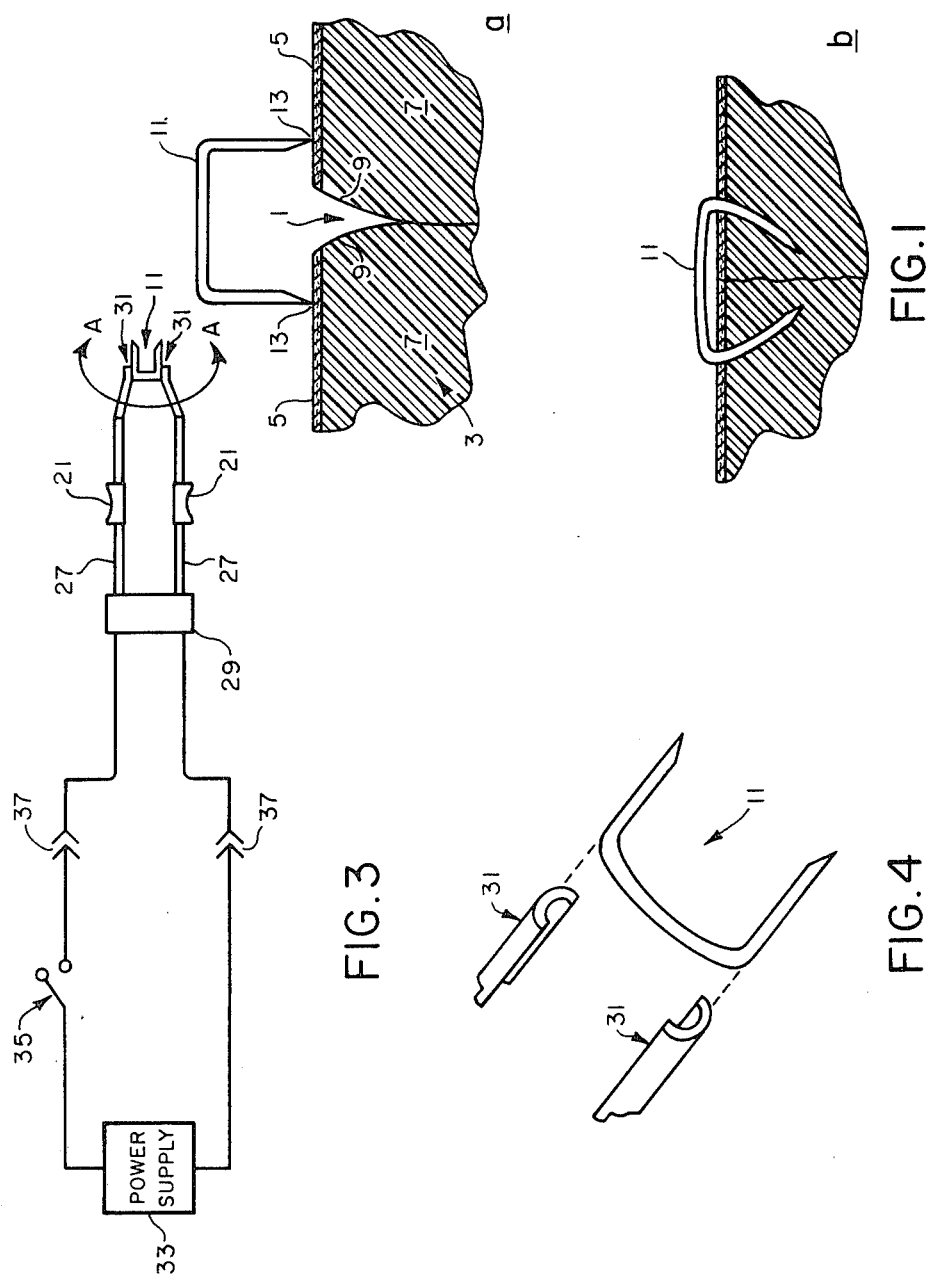

SHAPE-MEMORY SURGICAL STAPLE APPARATUS AND METHOD FOR USE IN SURGICAL SUTURING

BACKGROUND OF THE INVENTION

During recent decades, a growing portion of the suturing required in surgical operations has been done with surgical staples formed in a variety of shapes for tasks such as the ligation of tubular structures and the closure of surgical incisions. The staples have generally been formed of a stainless steel which is compatible with living tissue, such that they can remain in place indefinitely.

Surgical stapling has benefitted not only the surgeon, by relieving him of much tedious conventional suturing with needle and silk or gut thread, but also the patient, since staple-suturing can significantly shorten the time required to carry out an operative procedure. As a result, the quantity of anesthetic required can be reduced, and the operative shock effect on the patient's nervous system can be minimized. In short, the prospect for a successful and rapid recovery can be increased by adopting the more rapid technique of staple-suturing.

Despite these benefits, staple-suturing is not without its shortcomings. In particular, the staple applicators in use are generally rather heavy and often clumsy affairs which are tiring for the surgeon to use. Further they are more expensive than is desirable for two reasons: (a) the mechanisms are surprisingly complex and demand considerable precision in manufacture if they are to work satisfactorily; (b) each type of staple applicator is intended for a fairly narrow range of suturing tasks, i.e., is specialized such that the applicator designed for tubal ligation is not satisfactory for the suturing of incisions in skin or fascia. As a result the number of different types of such applicators needed multiplies the cost of providing such equipment in each operating room. Another problem with existing applicators is the difficulty of clearly seeing the point of application of the staple because of the sheer bulk of the staple applicator. Finally, the requirement to maintain stringently aseptic conditions during surgery means that the staple applicator must be subjected to sterilization before each use. This requirement amounts to an additional complication and an added cost.

The above and other drawbacks of the prior art staple suturing techniques result principally from the use of mechanically deformed staples made typically of stainless steel. Since the forces required to deform such staples into a desired closed shape are high, the staple applicator must be provided with a mechanism capable of generating such forces. Consequently, mechanisms employing either gas under pressure, or manually applied force multiplied by a mechanical system of high "mechanical advantage" are found in the prior art. Either approach requires that the large forces generated be applied to the staple in such a way as to deform it into precisely the desired closed shape. The shape required upon closure depends, of course, on the task for which the applicator is intended, such that the design of the applicator must be correspondingly different for the various suturing tasks.

As will appear from the remainder of this application, the above and many other persistent problems of the prior art staple-suturing methods and apparatuses could be solved if the means of deforming the staple from an open to a closed shape required the application of no more force than is required to hold the staple in position at the site of the suturing. Moreover, if the means of deforming the staple could be independent of the desired final shape of the staple, much of the burden of providing many different types of staple applicators for the different types of suturing could be eliminated.

SUMMARY OF THE INVENTION

The principal object of the present invention is to provide a method of staple-suturing in which the staples are caused to assume a closed position without the application of force.

A second object of the present invention is to provide a method of stape-suturing in which the means of effecting closure of the staples is not dependent on staple configuration either before or after closure.

A third object of the present invention is to provide a method of staple-suturing in which the closed position of the staple is predetermined during the process of manufacturing the staple.

A fourth object of the present invention is to provide a method of staple-suturing in which the means of causing closure of the staple is the application of heat thereto.

A fifth object of the present invention is to provide a surgical staple which may be supplied in an open position and which will assume a desired predetermined closed position upon the application of heat.

A sixth object of the present invention is to provide a surgical staple applicator which is inexpensive, lightweight and convenient in use.

A seventh object of the present invention is to provide a surgical staple applicator which is adapted to cause heating of the staples to effect closure thereof.

To the above ends, a surgical staple according to the present invention is made of a material possessing the property known as shape memory, such that it can be formed into any desired closed shape at a relatively high temperature, and subsequently deformed into a desired open shape at a relatively low temperature, and can be caused to revert to its predetermined closed shape upon subsequent heating.

A surgical staple applicator according to the present invention is provided with means to grip the staple to permit positioning the staple adjacent the site to be sutured, and means to heat the staple sufficiently to cause closure.

A surgical stapling method according to the present invention comprises gripping the staple with the staple applicator, positioning the staple adjacent to the site to be sutured, and heating the staple sufficiently to cause the staple to close, penetrate and clinch the tissues together.

The above and other features, objects and advantages of the present invention together with the best mode contemplated by the inventor for carrying out his invention will become more apparent from reading the following description of a preferred embodiment of the invention, and studying the drawings, in whicn:

BRIEF DESCRIPTION OF THE DRAWING

FIGS. 1a–b is a cross-sectional view showing a surgical staple according to the present invention before and after closure in the process of suturing an incision;

FIG. 3 is a view in partially schematic form of a surgical staple applicator apparatus according to the present invention;

FIG. 4 is a perspective detail view of the portion of FIG. 3 indicated by the arrows 4—4;

DETAILED DESCRIPTION OF A PREFERRED EMBODIMENT

Figure 5:
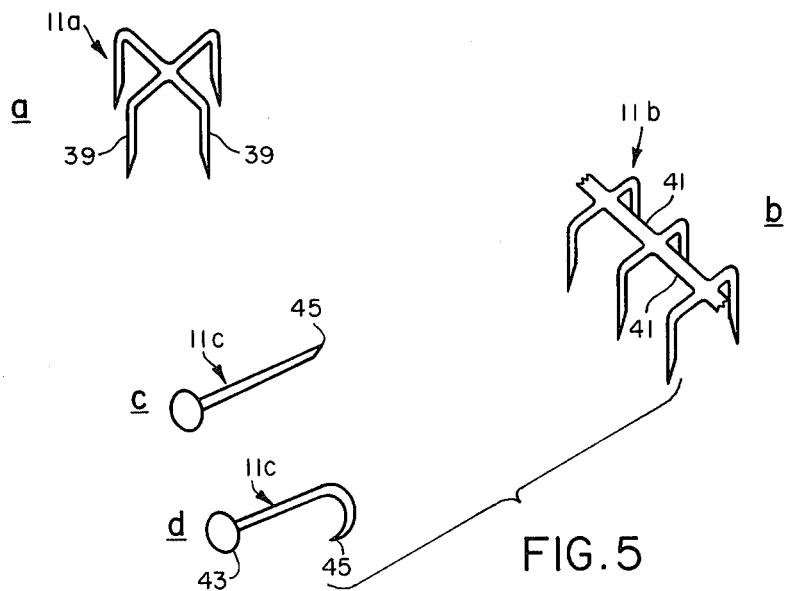
FIGS. 5a–d is a perspective view of alternate forms of the surgical staple according to the present invention.

In FIG. 1, 1 represents an incision or other breach in living tissue 3. Tissue 3 could be a surperficial portion of a human body, for example, and might be comprised of an epidermal layer 5 of skin and a subcutaneous layer 7 of adipose tissue. In order to promote the rapid healing and accurate reconstruction of the area around breach 1, the discrete portions into which breach 1 has divided the living tissue must be drawn together and held in intimate contact by some means of suturing. That is, an adequate means of suturing the tissues at the site of the breach must bring together the facing pair of disjoined edges 9 such that they are held in close contact and in the same relative alignment that existed prior to their disjoinder.

A surgical staple 11 according to the present invention is shown in FIG. 1a spanning breach 1, such that it is extending between the discrete portions of living tissue to be drawn together and joined. As shown, staple 11 is provided with a pair of pointed tip portions 13 which are in contact with tissue 3, ready to be inserted to fully close and suture breach 1. As shown in FIG. 1a, staple 11 is in an open position such that its tip portions 13 are relatively far apart.

In FIG. 1b, staple 11 is shown in an arcuate, closed shape in which it is fully inserted in suturing position, having drawn together the edges 9 in intimate contact and in accurate alignment. Although staple 11 has been illustrated as a simple beam, bent into the familiar U-shape employed for staples utilized for many non-surgical purposes, it is to be understood that such is for illustrative purposes only. In practice, staple 11 could have many different forms as will appear later in this application. Furthermore, the relative change in shape in the transition from open to closed position is to be understood to be selectable according to the degree of drawing together or clinching of the tissues which is needed.

Although mechanical means could be employed to cause staple 11 to undergo the change in shape required to penetrate and suture tissue 3 as illustrated in FIG. 1a–b, in accordance with the present invention, staple 11 is desirably made of a material having the property known as shape memory, such that staple 11 can be caused to undergo the change in shape merely by the application of heat.

Figure 2:
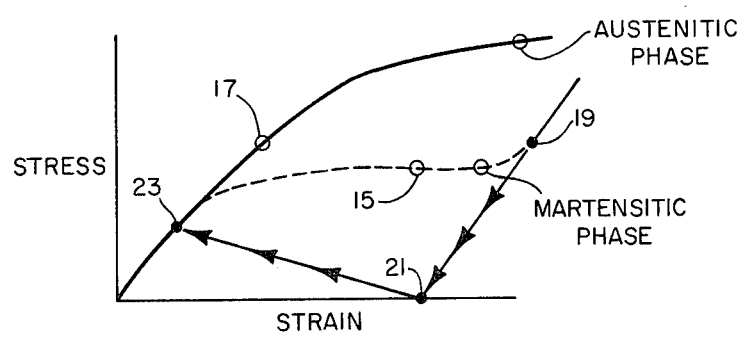
FIG. 2 is a stress-strain diagram showing the shape-memory characteristics of a special class of materials useful in forming staples according to the present invention.

Turning now to FIG. 2, a generalized stress-strain diagram of the class of materials known as shape-memory materials is illustrated. Such materials are characterized by having a low-temperature martensitic phase illustrated by characteristic 15 in FIG. 2, and a high-temperature austenitic phase illustrated by characteristic 17 in FIG. 2, and by the ability to transit between the very different physical characteristics of these two phases whenever their temperature passes through a certain transition temperature which is an intrinsic characteristic of the material.

In particular, if such materials are cooled below the transition temperature such that they are in the martensitic phase, and aree then stressed sufficiently to physically deform them into what is an apparently permanent new shape, upon heating above the transition temperature, all of the deformation which occurred in the martensitic phase will be reversed and the original shape will be recovered. That is, the deformed object will simply revert to the shape in which it existed prior to the cycle of cooling, deformation and reheating.

In accordance with the present invention, particularly good use if this characteristic can be made by fabricating surgical staples of such shape-memory materials. By forming the staples into any desired closed shape while the material is in the high-temperature austenitic phase, and subsequently cooling them below the transition temperature before deforming them into an open shape, the resulting staples will revert to the closed shape when reheated above the transition temperature. Moreover, in reverting to the closed shape above the transition temperature, the staples are capable of generating enough stress to easily penetrate and clinch together the tissues to be sutured.

In FIG. 2, the relationships between stress and strain which make such performance possible are clearly illustrated. If the staple has been formed of the material of FIG. 2 in any desired closed shape at a temperature above the transition temperature, it may be considered to be in a stress-strain condition represented by the origin in FIG. 2. If the material has been subsequently cooled below the transition temperature and then deformed into an open shape, the stress-strain relationship is depicted by characteristic 15, labeled "Martensitic Phase" in FIG. 2. Consequently, during the deformation into the open shape, the material of the staple undergoes increasing stress and strain until, at point 19, the resulting deformation is sufficient and the stress is removed. Stress thereupon goes to zero, and strain or deformation recovers by a small amount, leaving the material in the condition represented by point 21 in FIG. 2.

If the staple is subsequently reheated above the transition temperature such that the material is caused to enter the austenitic phase, strain will recover along the abscissa (which is the locus of zero stres conditions) until the austenitic phase characteristic 17 is reached, and would actually reach the origin in the total absence of any mechanical constraints.

However, some stress must be present in the staple during the process of penetrating and clinching together the tissues, and even after the staple is in place, resisting the compressive forces produced in the tissues at the suture site. This relatively low residual stress, and the corresponding residual strain are represented by point 23 on characteristic 17. As FIG. 2 shows, point 23 is actually quite close to the origin, such that the staple in this stress-strain condition has very nearly recovered fully to its initial closed state. Furthermore, this final arcuate closed shape of the staple can be varied as desired by selecting the cross-sectional dimensions of the beam from which the staple is formed, by selectively varying the closed shape of the staple when that shape is initially formed in the austenitic phase, and by appropriate selection of the particular shape-memory material used.

In this latter regard, satisfactory shape-memory materials for the fabrication of surgical staples must have transition temperatures in the range of 50–80 degrees Celsius, must be compatible with living tissue such that neither the staple nor the tissue is degraded by long mutual contact, and must have adequate mechanical properties to withstand stress levels encountered in suturing fascia as well as skin and other tissues.

I have found that binary and ternary compounds having approximately equal parts of nickel and titanium, and known generically under the tradename Nitinol are very satisfactory materials from which to manufacture shape-memory surgical staples. In particular, I have found that binary compositions having from 49.5 to 51.0 atomic % of nickel are useful in this application. However, if the achievement of a transition temperature in the range of 50–55 degrees Celsius rather than at a higher temperature is considered desirable, then the optimum composition of the binary compound is from 50.0 to 50.2 atomic % nickel, the balance titanium. Staples having this composition have transition temperatures of at least 50 degrees Celsius, such that they will not accidentally close at ambient temperatures normally encountered in shipment or storage. Neither do they require such a high temperature to cause closure that they might traumatize sensitive tissues unduly.

In FIG. 3, a surgical staple applicator apparatus for use in applying the staples of the present invention is illustrated. As shown, a surgical staple applicator 25 in the general form of a pair of tweezers forms the core of the apparatus. Applicator 25 has the general form of an elongate, hand-held body member, which in the particular form illustrated comprises a pair of elongated conductive beams 27 which are mounted in an insulative block 29 at one end, and which terminate in jaw portions 31 at the other end. Jaw portions 31 are suitably shaped to engage whatever form of surgical staple applicator 25 is intended to apply, and may if desired be interchangeable in order to accomodate a variety of staple types. However, applicator 25 is most desirably employed as a one-time use, disposable item, such that it can be supplied in a sterilized condition and need never be resterilized and reused. Therefore, applicator 25 will typically be supplied with fixed jaw portions 31 and adapted to engage the particular type of staple in use.

As shown in FIG. 3, the applicator 25 is provided with jaw portions 31 adapted for holding the familiar U-shaped staples 11', which are to be provided in a presterilized package (not shown) from which they are removed one-at-a-time by the simple expedient of grasping them with jaw portions 31 and immediately transporting them to the suturing site without ever bringing them in contact with any contaminating object.

FIG. 4 details the particular form of jaw portion 31 which is adapted for engaging U-shaped staples 11'. In FIG. 4, jaw portions 31 are shown to be in the form of open channels of generally semicircular cross section, oriented to have their open sides in facing opposition to one another across a gap within which staple 11' is received. As Staple 11' is gripped and held by jaw portions 31, with the outer surfaces of the staple in contact with jaw portions 31.

Returning to FIG. 3, applicator 25 is provided with a pair of finger grips 27 which permit the surgeon to grasp the applicator between thumb and index finger for example, and apply sufficient pressure to maintain firm engagement and contact between jaw portions 31 and staple 11' in use. Grips 27 may be made of a plastic such as a polycarbonate which is simultaneously molded and bonded to beams 27. Similarly, insulative block 29 may also be of a plastic material which is molded about and bonded to beams 27. Beams 27 must be dimensioned to be rigid enough to withstand normal handling, yet compliant enough to easily permit the slight deflection needed to grasp staple 11'. Suitable materials for the fabrication of beams 27 are aluminum, stainless steel, or beryllium copper.

As already noted, the application of heat sufficient to raise the temperature of staple 11' above the transition temperature of the shape-memory material concerned will cause closure of the staple. In the apparatus of FIG. 3, the means for applying this small amount of heat has been provided in the form of an electrical power supply 33 which might be a low voltage D.C. supply, such as a battery providing from 1.5 to 12 volts.

Power supply 33 is connected to each of beams 27 of applicator 25 by means of a simple series circuit which is closed by actuating a normally open switch 35. Switch 35 may be realized in practice most conveniently by a foot switch, such that the surgeon's hands are left free to control the suturing operation. By means of a connector 37, the applicator may be disconnected from its source of power when the suturing operation is complete.

In use, the surgeon removes applicator 25 from its sterile package, connects its electrical leads to power supply 33 by means of connector 37, grasps a sterile surgical staple 11' in jaw portions 31, moves the staple to the suturing site and positions the staple spanning a breach in the tissues to be sutured as shown in FIG. 1a. He then closes switch 35 to cause current to flow through the electrical circuit, which is completed by staple 11'. The passage of this current is accompanied by the production of Joule heat in the staple as is well known. Since the staple is the most resistive part of the circuit, substantially all the heat generated by the passage of the current will be concentrated in the staple.

As soon as the staple has warmed sufficiently that its temperature has reached the transition temperature, it closes, penetrating and suturing the tissues as shown in FIG. 1b. As the staple closes, it simultaneously withdraws from the tip portions 31, such that when the staple is fully in suturing position, applicator 25 is removed, terminating the flow of current.

In FIG. 5, alternative forms of staples according to the present invention are shown. FIG. 5a illustrates a radially closing staple 11a, which would be useful in closing and suturing a generally round breach in living tissue, such as might result from a puncture wound, for example. As shown, staple 11a consists essentially of a pair of beams 39, integrally joined at their midpoint and oriented such that the principal axes of the two beams are angularly spaced, typically by 90 degrees, such that the beams are mutually orthogonal. As also shown in FIG. 5a, the two beams 39 have the same U-shape as found in the staple 11 in FIG. 1.

FIG. 5b shows how an elongated, multiply pronged staple 11b might be provided in a form for conveniently closing a long straight incision. Staple 11b may be of any convenient length, as indicated by the broken lines, and is formed essentially of parallel pairs of beams integrally joined at their midpoints by links 41.

FIG. 5c–d illustrates a staple 11c especially adapted for a "tacking" operation, in which two overlapping tissue structures are to be joined together. As shown in FIG. 5c–d, the staple is provided in a straight nail form when in open position, and closes to a "clinch nail" shape when in place. Accordingly, staple 11c is provided with an enlarged head 43 at one end, and with a pointed tip 45 at the other end. However, staple 11c is fundamentally formed as a beam and in use is positioned extending between and in contact with the tissues to be joined by being inserted through them. Upon the application of sufficient heat to cause closure of staple 11c, this beam curves into the closed shape illustrated in FIG. 5d, such that the tip 45 points generally toward the enlarged head 43, drawing the tissues together and joining them.

It is to be understood that in practice, each of the alternate staples shown in FIG. 5 would require a somewhat different form of jaw portion 31 from the shape which has been illustrated in FIGS. 3 and 4. However, the appropriate jaw shape is relatively easy to devise from a consideration of the requirement that the jaw portion must engage each of the types of staples.

Although I have described my invention with some particularity in reference to a set of illustrations which, taken together, comprise a preferred embodiment representing the best mode known to me for carrying out my invention, those skilled in the art will realize that many modifications could be made, and many alternative embodiments thus derived without departing from the scope of my invention. Consequently, the scope of the invention is to be determined only from the following claims.

What is claimed is:

1. A method of drawing together and joining in intimate contact discrete portions of living tissue, comprising the steps:
    (a) providing a surgical staple made of a shape-memory material, said staple being formed into a closed shape at a temperature above the transition temperature of said material, and subsequently deformed into an open shape at a temperature below said transition temperature;
    (b) engaging the open staple by a mechanical jaw and positioning the open staple to extend between, and be in contact with each of said portions of living tissue;
    (c) heating said staple by passing a electric current therethrough from the jaw to elevate the staple to a temperature above the transition temperature to close the staple, drawing together and joining the tissue.

2. A surgical stapling apparatus for use in applying shape-memory surgical staples of the kind which close when heated sufficiently to reach a temperature equal to or greater than a certain intrinsic transition temperature of the staple material, to thereby draw together and join in intimate contact discrete portions of living tissue, comprising in combination:
    (a) an elongate, hand-held body member;
    (b) jaw means on said body member to engage and hold a surgical staple; and
    (c) means to selectively apply heat to said staple to effect closure thereof.

3. The stapling apparatus according to claim 2 wherein said means to apply heat comprises means to cause an electrical current to pass through said staple to cause Joule heating thereof.

4. The stapling apparatus according to claim 2 wherein said jaw means comprises a plurality of conductive jaw portions mutually insulated from one another, and oriented in facing opposition to one another across a gap, said jaw portions being selectively movable toward one another to grip and hold a surgical staple in said gap.

5. The stapling apparatus of claim 4 wherein said jaw portions are electrically conductive, and further including means to energize said jaw portions wiht a source of electrical potential difference to cause an electric current to flow in said staple to thereby cause Joule heating of said staple.

6. The stapling apparatus of claim 5 wherein said body member comprises a pair of resilient electrically conductive beams, said beams being mechanically joined together at one common end thereof by an insulative block, said beams extending in spaced side-by-side relation away from said block, and terminating at their other ends in said jaw portions, and means on each of said beams to permit connection to an external source of electrical potential difference.

7. A surgical staple for insertion in and holding together discrete regions of at least one member comprising:
    a first beam made of a material having the property known as shape memory such that said material exists in a first phase at first temperatures below an intrinsic phase-transition temperature, and exists in a second phase at second temperatures above said phase-transition temperature, said shape-memory property being manifested by the ability of said material when inelastically deformed at a temperature below said transition temperature to recover to its undeformed shape upon subsequent heating to a temperature above said transition temperature;
    said beam existing in a closed shape at one of said temperatures for holding together said discrete regions and existing in an open shape at the other of said temperatures, one of said shapes being its deformed shape;
    whereby when during use said staple is positioned extending between, and in contact with, said discrete regions in one of said shapes, said staple is caused to recover to the other of said shapes, upon heating of said staple to a temperature above said transition temperature wherein said staple is generally nail-shaped, and comprises: an enlarged heat portion at one end of said beam, and a generally pointed tip portion at the other end of said beam.

8. The surgical staple of claim 7 wherein said beam is generally straight when in said open shape, and wherein said beam is so curved in said closed shape as to cause said tip portion to be oriented in a direction generally towards said head portion.

9. A surgical staple for insertion in and holding together discrete regions of at least one member comprising:
    a first beam made of a material having the property known as shape memory such that said material exists in a first phase at first temperature below an intrinsic phase-transition temperature, and exists in a second phase at second temperatures above said phase-transition temperature, said shape-memory property being manifested by the ability of said material when inelastically deformed at a temperature below said transition temperature to recover to its undeformed shape upon subsequent heating to a temperature above said transition temperature;
    said beam existing in a closed shape at one of said temperatures for holding together said discrete regions and existing in an open shape at the other of said temperatures, one of said shapes being its deformed shape;

whereby when during use said staple is positioned extending between, and in contact with, said discrete regions in one of said shapes, said staple is caused to recover to the other of said shapes, upon heating of said staple to a temperature above said transition temperature, and further including a second beam made of said shape-memory material, said first and second beams being integrally joined.

10. The surgical staple of claim 9 wherein said beams are integrally joined generally midway along their respective lengths, and are mutually oriented with their principal axes angularly spaced from one another.

11. The surgical staple of claim 10 wherein said beams are generally U-shaped when in said open shape, and wherein said principal axes are substantially orthogonal to one another.

12. The surgical staple of claim 9 further including a link integrally joined to each of said beams to thereby interconnect them.

13. The surgical staple of claim 12 wherein said link integrally joins each of said beams generally midway therealong, and wherein said beams are oriented generally mutually parallel.

14. The surgical staple of claim 7 or 9 wherein said closed shape of said beam for holding together said discrete regions is its undeformed shape and its open shape is its deformed shape.

* * * * *